United States Patent [19]

Watanabe et al.

[11] Patent Number: 5,051,185

[45] Date of Patent: Sep. 24, 1991

[54] ABSORBENT OF $\beta_2$-MICROGLOBULIN

[75] Inventors: Hiroyuki Watanabe; Tadashi Yokoyama; Naokuni Yamawaki, all of Shizuoka, Japan

[73] Assignees: Asahi Kasei Kogyo K.K., Osaka; Asahi Medical Co., Ltd., Tokyo, both of Japan

[21] Appl. No.: 512,629

[22] Filed: Apr. 19, 1990

Related U.S. Application Data

[63] Continuation of Ser. No. 266,614, Nov. 3, 1988, abandoned.

[30] Foreign Application Priority Data

Nov. 6, 1987 [JP] Japan .................................. 62-279376
Aug. 8, 1988 [JP] Japan .................................. 63-196197
Aug. 18, 1988 [JP] Japan .................................. 63-203776

[51] Int. Cl.[5] ............................................ B01D 15/08
[52] U.S. Cl. .................................... 210/635; 210/679; 210/692; 210/502.1; 210/905; 502/402; 502/403; 502/404; 525/54.1; 530/354; 530/356; 530/394; 530/413; 530/415; 530/813; 530/815
[58] Field of Search ............... 210/635, 660, 679, 690, 210/691, 502.1, 905, 692; 502/401, 402, 403, 404; 530/394, 412, 415, 354, 356, 811, 813, 814, 815, 413; 525/54.1; 604/4, 5, 6

[56] References Cited

U.S. PATENT DOCUMENTS 4,171,283 10/1979 Nakashima et al. ............. 210/502.1
4,411,532 10/1983 Cuatrecasas et al. ............. 536/55.1
4,721,730 1/1988 Furuyoshi et al. ................. 210/679

FOREIGN PATENT DOCUMENTS 0225867 12/1983 European Pat. Off. ..
0236509 9/1986 European Pat. Off. ..
0247592 5/1987 European Pat. Off. ..
63-15960 1/1988 Japan ............................. 210/502.1
63-19154 1/1988 Japan ............................. 210/502.1
63-19155 1/1988 Japan ............................. 210/502.1

OTHER PUBLICATIONS

4535 A.S.A.I.O. Transactions, 33(1987) Sep., No. 3 Removal of Beta-2-Microglobulin by Direct Hemoperfusion with a Newly Developed Absorbent, Akizawa et al.
Chemical Abstract vol. 109, 1988.

Primary Examiner—W. Gary Jones
Attorney, Agent, or Firm—Sughrue, Mion, Zinn Macpeak & Seas

[57] ABSTRACT

An adsorbent for $\beta_2$-microglobulin is disclosed, which comprises a water-insoluble carrier having supported thereon, as a ligand, at least one electrolyte selected from the group consisting of a polyamino acid, a polysaccharide, a synthetic high polymer, collagen having an isoelectric point of 9.5 or more, and gelatin having an isoelectric point of 6.5 or more, wherein said electrolyte has a molecular weight not less than 1,000 and an X value of more than 2.0, wherein X is a relationship regarding the skeleton structure of said electrolyte and is the sum of A and B, wherein A represents (the number of carbon atoms of the skeleton structure)−(the number of hydrophilic groups)/(the number of hydrophilic groups); and B represents |(the number of cationic groups)−(the number of anionic groups)|/(the number of hydrophilic groups). The adsorbent exhibits adsorptivity for $\beta_2$-microglobulin at high efficiency and high selectivity.

26 Claims, 2 Drawing Sheets

FIG.2

ABSORBENT OF $\beta_2$-MICROGLOBULIN

This a continuation of application Ser. No. 07/266,614 filed Nov. 3, 1988, now abandoned.

FIELD OF THE INVENTION

This invention relates to an adsorbent for cleaning body fluids, such as blood, plasma, serum, ascites, hydrothrax, etc., by selectively adsorbing and removing a malignant substance relative to diseases. More particularly, it relates to an adsorbent having a specific affinity for $\beta_2$-microglobulin which is found in high level in body fluids of patients suffering from renal insufficiency or malignant tumor and causes flexor canal syndrome, amyloidosis, digitus recellens, gonalgia, pruritus, bone involvement, and the like.

BACKGROUND OF THE INVENTION

Blood dialysis for patients suffering from renal insufficiency has been carried out for about 10 years, and abnormalities, such as flexor canal syndrome, have been revealed. In recent years, it has turned out that such abnormalities are caused by $\beta_2$-microglobulin. $\beta_2$-microglobulin is relatively hard to remove by dialysis and various symptoms are manifested through accumulation of this substance within the body.

Blood filtration and dialytic filtration have conventionally been employed for the purpose of removing such a medium-molecular weight substance. These techniques, however, attain low rates of removal and require a large quantity of a replenisher for achieving effective removal. Although the rate of removal may be increased by making the pores of the membrane employed larger, a small increase in pore size results in loss of albumin, a useful protein. Under the present situation, therefore, control of pore size cannot achieve effective and selective removal of medium-molecular weight substances.

JP-A-62-240068 (the term "JP-A" as used herein refers to a "published unexamined Japanese patent application") discloses an adsorbent for $\beta_2$-microglobulin, but the adsorption performance of this adsorbent is insufficient. Further, JP-A-62-204761 discloses various adsorbents for in vitro circulation which comprise a carrier having supported thereon a ligand. However, this reference does not refer to an adsorbent for $\beta_2$-microglobulin.

SUMMARY OF THE INVENTION

One object of this invention is to provide an adsorbent which can be generally put into wide use for selectively adsorbing $\beta_2$-microglobulin at high efficiency without involving nonspecific adsorption of other useful proteins, particularly albumin.

Another object of this invention is to provide an adsorbent for cleaning or regenerating body fluids, such as whole blood or blood plasma, which needs no replenishment of the body fluids, has safety and can be sterilized easily.

In the light of the above-described problems associated with the conventional techniques for cleaning body fluids by the use of high molecular membranes, it has been found in the present inention that an adsorbent containing on its surface an electrolyte selected from specific polyamino acids, polysaccharides, synthetic high polymers, collagen having an isoelectric point of 9.5 or more, and gelatin having an isoelectric point of 6.5 or more (hereinafter referred to as "specified electrolyte") adsorbs $\beta_2$-microglobulin at a surprisingly high efficiency. It has been confirmed in the present invention that such selective and highly efficient adsorption of $\beta_2$-microglobulin can be achieved as long as the specified electrolyte has a specific molecular weight and a skeleton structure whose carbon atom number, hydrophilic group number and ionic group number satisfy a specific relationship. The present invention has thus been completed based on these findings.

More specifically, the present invention relates to an adsorbent for $\beta_2$-microglobulin which comprises a water-insoluble carrier having supported thereon, as a ligand, at least one electrolyte selected from the group consisting of a polyamino acid, a polysaccharide, a synthetic high polymer, collagen having an isoelectric point of 9.5 or more, and gelatin having an isoelectric point of 6.5 or more, wherein said electrolyte has a molecular weight not less than 1,000 and an X value of more than 2.0, wherein X is a relationship regarding the structure of the skeleton of the electrolyte and is the sum of A and B, wherein A represents (the number of carbon atoms of the skeleton structure) − (the number of hydrophilic groups)/(the number of hydrophilic groups); and B represents (the number of cationic groups) − (the number of anionic groups) /(the number of hydrophilic groups).

DETAILED DESCRIPTION OF THE INVENTION

The $\beta_2$-microglobulin adsorbent according to the present invention comprises a water-insoluble carrier on which the specified electrolyte is fixed by any means, such as an epichlorohydrin method or a cyanogen halide method. It is preferable that the electrolyte extends from the carrier and is fixed as a ligand rather than flatly covering the surface of the water-insoluble carrier. This is because such a fixing mode acquires a larger surface area of the adsorbent to be in contact with $\beta_2$-microglobulin so as to ensure efficient adsorption of $\beta_2$-microglobulin.

The terminology "$\beta_2$-microglobulin" as used herein means $\beta_2$-microglobulin usually measurable by an enzymatic immunoassay, etc., in clinical examinations. More specifically, $\beta_2$-microglobulin has the following physical properties:
Sedimentation Constant: 1.6S
Partial Specific Volume: 0.72 to 0.73 ml/g
Molecular Weight: 11,000 to 12,000
Nitrogen Content: 16 to 17%

The $\beta_2$-microglobulin to which the present invention is applicable includes not only $\beta_2$-microglobulin itself but combinations with other proteins and $\beta_2$-microglobulin in which the sequence of amino acid is partially altered.

The electrolyte which can be fixed on the surface of the water-insoluble carrier as a ligand is specified by X defined by the equation shown below, which satisfies a relationship among the numbers of carbon atoms, hydrophilic groups, cationic groups, and anionic groups contained in the skeleton structure of the specified electrolyte.

$X = A + B$ wherein A represents (the number of carbon atoms of the skeleton structure)−(the number of hydrophilic groups)/ (the number of hydrophilic groups); and B represents |(the number of cationic groups)−(the number of anionic groups)|/(the number of hydrophilic groups).

The term "number of carbon atoms of the skeleton structure" means the number of all of the carbon atoms in the chemical structure inclusive of the main chain and side chains of the specified electrolyte other than those contained in the characteristic groups carrying a negative charge, i.e., carboxyl groups. The carbon atom in a carboxyl group is excluded because it is hydrophilic and chiefly shows only the effects of a negative charge. Carbon atoms of characteristic groups other than a carboxyl group, e.g., alkoxy, aldehyde, alkoxycarbonyl, and amido groups, are counted.

The term "number of hydrophilic groups" as used herein means the number of all of the polar characteristic groups in the chemical structure inclusive of the main chain and side chains which show strong interaction with water, such as a carboxyl group ($COO^-$, $COOH$, $COONa$), a sulfo group ($SO_3^-$, $SO_3H$, $SO_3Na$), a phospho group ($PO_3^-$, $PO_3H$, $PO_3Na$), a primary, secondary, tertiary, or quaternary amino group, a hydroxyl group (OH), etc.

The term "number of cationic groups" as used herein means the number of all of the characteristic groups in the chemical structure inclusive of the main chain and side chains which show a positive charge in a neutral electrolytic solution, e.g., blood or the like body fluids, such as a primary, secondary, tertiary or quaternary amino group.

The term "number of anionic groups" as used herein means the number of all of the characteristic groups in the chemical structure inclusive of the main chain and side chains which show a negative charge in a neutral electrolytic solution, e.g., blood or the like body fluids, such as a carboxyl group ($COO^-$, $COOH$, $COONa$), a sulfo group ($SO_3^-$, $SO_3H$, $SO_3Na$), a phospho group ($PO_3^-$, $PO_3H$, $PO_3Na$), etc.

It is essential in the present invention that X as defined above is more than 2.0, preferably between and 50, more preferably between 4 and 25, and most preferably between 5 and 15. If X is not more than 2, the interaction between the specified electrolyte and $\beta_2$-microglobulin is too weak to exhibit sufficient adsorptivity for $\beta_2$-microglobulin.

The adsorptivity for $\beta_2$-microglobulin is believed to be ascribable to synergistic effects of A and B. A (i.e., the ratio of the difference between the number of carbon atoms and the number of hydrophilic groups to the number of hydrophilic groups) seems to depict a hydrophobic interaction exerted between the specified electrolyte and $\beta_2$-microglobulin. B (i.e., the ratio of an absolute difference betwen the number of cationic groups and the number of anionic groups to the number of hydrophilic groups) seems to depict an ionic interaction exerted between the specified electrolyte and $\beta_2$-microglobulin. It is considered that the synergistic effect of A and B, that is, synergism of the hydrophobic interaction of A and the ionic interaction of B, enhances the interaction between the specified electrolyte and $\beta_2$-microglobulin to thereby increase adsorptivity for $\beta_2$-microglobulin and, at the same time, improve selectivity to $\beta_2$-microglobulin (non-adsorptivity for substances other than $\beta_2$-microglobulin, e.g., albumin).

The electrolyte which can be fixed on the water-insoluble carrier as a ligand may be any of polyamino acids, polysaccharides, synthetic high polymers, collagen having an isoelectric point of 9.5 or more, and gelatin having an isoelectric point of 6.5 or more, each having a molecular weight of 1,000 or more, containing at least one characteristic group showing a positive or negative charge in a neutral electrolytic solution (e.g., blood and other body fluids) in the molecule thereof, and having X of more than 2.0.

The polyamino acids which can be used in the present invention are represented by formula:

wherein m is an integer of 30 or less; n is an integer of 2 or more; and $R_1$, $R_2$, ..., and $R_m$, which may be the same or different, each represents a side chain of natural amino acids constituting proteins.

Specific examples of the polyamino acids include polymers of aliphatic amino acids containing a carboxyl group, a primary or secondary amino group, etc., as a characteristic group having a negative or positive charge, such as polyaspartic acid, polyglutamic acid, polylysine, polyhydroxylysine, etc.; copolymers of aliphatic amino acids containing a carboxyl group, a primary or secondary amino group, etc., as a characteristic group having a negative or positive charge and aliphatic amino acids, such as poly(glutamic acid-alanine), poly(glutamic acid-lysine), poly(aspartic acid-lysine), poly(lysine-phenylalanine), poly(lysine-tryptophane), poly(glutamic acid-lysine-tyrosine), poly(glutamic acid-tyrosine-alanine), etc.; copolymers of aliphatic amino acids and other amino acids, e.g., aromatic amino acids; polymers of heterocyclic amino acids containing a tertiary or quaternary amino group, etc., as a characteristic group having a positive charge, such as polyhistidine; copolymers of heterocyclic amino acids containing a tertiary or quaternary amino group as a characteristic group having a positive charge and heterocyclic amino acids, such as poly(histidine-proline), poly(histidine-tryptophane); and copolymers of heterocyclic amino acids and other amino acids, e.g., aromatic amino acids, such as poly(histidine-phenylalanine), poly(histidine-tyrosine). Preferred of them are copolymers of aliphatic amino acids containing a carboxyl group as a characteristic group having a negative charge and aliphatic amino acids, such as poly(glutamic acid-alanine), poly(glutamic acid-tyrosine) and poly(glutamic acid-alanine-tyrosine); and copolymers of aliphatic amino acids and aromatic amino acids having a benzene ring.

The polysaccharides which can be used in the present invention include homopolysaccharides and heteropolysaccharides as classified according to the nomenclature established based on the agreement between IUPAC (International Union of Pure and Applied Chemistry) and IUB (International Union of Biochemistry) in 1969 (cf. *J. Biol. Chem.*, Vol. 247, 613-634 (1972)).

Specific examples of the polysaccharides are homopolysaccharides having introduced therein a characteristic group having a positive charge (e.g., dimethylaminoethyl group), such as xylan, amylase, glycogen, dextran, prulan, agraose, mannan, inulin, chitin, etc.;

and heteropolysaccharides having introduced therein a characteristic group having a positive charge (e.g., dimethylaminoethyl group, diethylaminoethyl group), such as chondroitin, chondroitin sulfate, hyaluronic acid, heparin, gum arabic, etc. Preferred among them are homopolysaccharides having introduced therein a characteristic group having a positive charge (e.g., dimethylaminoethyl group, diethylamino group), such as dimethylaminoethyl-dextran, diethylaminoethyldextran, etc.

The synthetic high polymers which can be used in the present invention include homo- or copolymers of monomers whose main chain solely consists of carbon atoms and these homo- or copolymers having introduced therein a characteristic group (e.g., a carboxyl group, a sulfo group, an amino group).

Specific examples of these synthetic high polymers are polymers of vinyl compounds containing a carboxyl group or a sulfo group as a characteristic group having a negative charge, such as polymethacrylic acid and sulfonated polystyrene, etc.; and copolymers of vinyl compounds and vinyl compounds containing a carboxyl group as a characteristic group having a negative charge, such as propylene-acrylic acid copolymer, butadiene-acrylonitrile-acrylic acid copolymer, ethylene-methacrylic acid copolymer, methyl methacrylate-methacrylic acid copolymer, acrylonitrile-maleic anhydride copolymer, butadiene-maleic anhydride copolymer, methyl vinyl ether-maleic anhydride copolymer, styrene-maleic acid copolymer, etc.

Preferred of them are polymers of vinyl compounds containing a characteristic group having a negative charge and a benzene ring and copolymers of vinyl compounds containing a benzene ring and vinyl compounds containing a characteristic group having a negative charge, such as sulfonated polystyrene and styrene-maleic acid copolymer.

Further, polymers of vinyl compounds containing an amino group (e.g., a tertiary or quaternary amino group) as a characteristic group having a positive charge and a benzene ring, such as polyvinylpyridine, poly(N-alkyl-4-vinylpyridinium chloride), polyvinylbenzyltrimethylammonium chloride, etc., can also be used.

Furthermore, polymers or copolymers of vinyl compounds containing both a characteristic group having a positive charge and a characteristic group having a negative charge, such as methacrylic acid-dimethylaminoethyl methacrylate copolymer, sulfonated styrene-N-alkyl-4-vinylpyridinium chloride copolymers, poly-4-vinyl-N-alkylsulfonate pyridinium, etc., can also be used.

Collagen which can be used in the present invention includes any type of collagen as long as it has a molecular weight of 1,000 or more, X of more than 2.0, and an isoelectric point of not less than 9.5.

The terminology "isoelectric point" as used herein is to specify the collagen fixed on the surface of the water-insoluble carrier and can be determined by electrophoresis analysis as described, e.g., in Nippon Seikagaku (ed.), *SEIKAGAKU JIKKEN KOZA 1, TANPAKU-SHITSU NO KAGAKU I,* 305–312, Tokyo Kagaku Dojin (Mar. 30, 1977). The collagen to be used in this invention should have an isoelectric point of not less than 9.5, preferably in the range of from 9.8 to 12.0, and more preferably in the range of from 10.0 to 11.0. If the isoelectric point is less than 9.5, the interaction with $\beta_2$-microglobulin is so weak that the adsorbent having collagen on the surface thereof exhibits low adsorptivity for $\beta_2$-microglobulin. It is believed that collagen having the above-specified isoelectric point exhibits a strong positive charge in a neutral electrolytic solution, e.g., blood and other body fluids. In other words, since the collagen carries a larger number of cationic groups (i.e., ionic groups showing a positive charge in a neutral electrolytic solution, e.g., a primary, secondary, tertiary or quaternary amino group) than anionic groups (i.e., ionic groups showing a negative charge in a neutral electrolytic solution, e.g., a carboxyl group), the ionic interaction with $\beta_2$-microglobulin is enhanced whereby the resulting adsorbent exhibits increased adsorptivity for $\beta_2$-microglobulin and also improved selectivity to $\beta_2$-microglobulin over other substances, e.g., albumin.

The collagen to be applied for the present invention includes various types of collagen obtained by processing the skin, bones, tendons, blood vessels, basement membranes, placenta, muscles, cartilages, etc., of various animals, e.g., human, cattles, pigs, etc., with enzymes, acids, alkalis, etc., and chemically modifying the resulting collagen (inclusive of collagen whose telopeptide at the terminal is severed, i.e., atelocollagen) with an organic alcohol, e.g., methanol, ethanol, isopropyl alcohol, etc. The above-described processing of animal tissues is described, e.g., in Y. Nagai and D. Fujimoto (ed.), *COLLAGEN TAISHA TO SHIKKAN,* 110-133, Kodansha (Apr. 1, 1982), and H. Noda, Y. Nagai, and D. Fujimoto (ed.), *Collagen,* 196–206, Nankodo (May 10, 1978). Among them preferred is methylated atelocollagen Type I, which is obtained by treating a carboxyl group (—COOH) in the side chain of aspartic acid and glutamic acid constituting atelocollagen Type I with methanol to convert it to —COOOCH$_3$.

The gelatin which can be used in the present invention includes any type of gelatin as long as it has a molecular weight of 1,000 or more, X of more than 2.0, and an isoelectric point of 6.5 or more, preferably in the range of from 7.0 to 11.0, and more preferably in the range of from 8.0 to 10.0.

If the isoelectric point of glatin is less than 6.5, the interaction with $\beta_2$-microglobulin is too weak to exhibit sufficient adsorptivity for $\beta_2$-microglobulin. The isoelectric point of gelatin is considered to have the same significance as elucidated above with respect to collagen.

The gelatin to be used includes those obtained by heat treating the above-described collagen in an acidic or alkaline condition, those obtained by further treating the thus-obtained gelatin with an organic alcohol (e.g., methanol, ethanol, isopropyl alcohol) to esterify carboxyl groups of aspartic acid and glutamic acid constituting the gelatin, and those obtained by repolymerizing the gelatin (obtained by the above-described heat treatment of collagen) with isocyanates. Preferred of them are those obtained by heat treating collagen (obtained by treating under an acidic condition) under an acidic condition.

These specified electrolytes have a weight average molecular weight of 1,000 or more, preferably in the range of from 2,000 to 1,000,000, more preferably from 5,000 to 500,000, most preferably from 10,000 to 200,000, as determined based on the principle of light scattering as described in Nippon Kagakukai (ed.), *SHIN JIKKEN KAGAKU KOZA* 19, *KOBUNSHI II,* 514–518, Maruzen Co., Ltd. (Sept. 20, 1978). If the molecular weight is smaller than 1,000, the electrolyte fixed on the surface of the water-insoluble carrier has too short a molecular chain, thus failing to adsorb a sufficient amount of $\beta_2$-micorglobulin. Therefore, in order to effectively adsorb a sufficient amount of $\beta_2$-microglobulin, the electrolyte is required to have a molecular weight of at least 1,000.

The water-insoluble carrier which can be used in the present invention is not particularly limited as long as it is capable of fixing the specified electrolyte thereon, and includes organic high molecular compounds and inorganic compounds, such as cellulose derivatives, vinyl polymers, polyacrylamides, polyhydroxyethylmethyl acrylate, glass, silica, etc.

In order to achieve highly efficient and selective adsorption of $\beta_2$-microglobulin and particularly for use in cleaning whole blood containing hemocytes such as blood platelets, it is preferable that the water-insoluble carrier has a double-layered structure composed of a water-insoluble material having a contact angle with air bubble in water of at least 20° and a polymer compatible with blood (hereinafter referred to as "blood-compatible polymer").

The terminology "contact angle" as used herein means a contact angle formed between the surface of a solid and an air bubble on the surface in water which is measurable according to the principle and method disclosed in W. C. Hamilton, *J. Colloid Interface Sci.*, Vol. 40, 219-222 (1972) and J. D. Andrade, *J. Polym. Sci. Polym. Symp.*, Vol. 66, 313-336 (1979). A contact angle of a liquid droplet on the surface of a solid in air, which is commonly adopted as a physical property, is not suitable for specifying water-absorbing materials since such a contact angle is subject to changes with time. In the present invention, the measurements of the contact angle were conducted at 25° C. ten times for each sample in the form of a sheet or film, and the average of the measured values was obtained.

The water-insoluble material to be used in the double-layered carrier may be any of inorganic compounds and organic high molecular compounds as long as it has a contact angle of at least 20°. From the standpoint of compatibility of the blood-compatible polymer and the water-insoluble material, and safety of eluates from the carrier, organic high molecular compounds are preferred.

In view of compatibility of the blood-compatible polymer and the water-insoluble material, the organic high molecular compounds to be used as the water-insoluble carrier has a contact angle of at least 20°, preferably at least 30°, and more preferably at least 40°.

Examples of preferred organic high molecular compounds are polyolefin compounds (e.g., polyethylene, polypropylene, polytetrafluoroethylene), polymers of vinyl compounds (e.g., polystyrene, polymethacrylates, polyacrylates), polyamide compounds (e.g., nylon 6, nylon 66), polyester compounds (e.g., polyethylene terephthalate), and the like. More preferred of them are homopolymers of methacrylates, acrylates, styrene or styrene derivatives and copolymers of these monomers, comonomers, and a crosslinking agent. In particular, crosslinked polymer particles mainly comprising methyl methacrylate or styrene are preferred. Any of known crosslinking agents may be used. Examples of usable crosslinking agents include divinylbenzene, ethylene glycol di(meth)acrylate, polyethylene glycol di(meth)-acrylate, etc.

The above-referred blood-compatible polymer may be any of known materials compatible with blood as long as it is capable of fixing the specific electrolyte according to the present invention thereon. From the viewpoint of preventing fromation of fine particles, that is, facilitating coating of the water-insoluble material, safety, and sterility, preferred examples of the blood-compatible polymes are (meth)acrylate polymers, acrylamide polymers, polyvinylpyrrolidone polymers, polyvinyl alcohol polymers, ethylene-vinyl alcohol copolymers, ethylene-vinyl acetate copolymers, cellulose nitrate, gelatin, and the like.

For the purpose of preventing formation of fine particles and further improving compatibility with blood, polymers containing a nitrogen-containing basic functional group are particularly preferred as the blood-compatible polymer.

The above-referred "nitrogen-containing basic functional group" means a functional group having a positive charge on its nitrogen atom in an acidic aqueous solution to form a cation. Such a functional group includes a primary amino group, a secondary amino group, a tertiary amino group, a quaternary amino group, and a nitrogen-containing aromatic cyclic group (e.g., pyridyl group, imidazolinyl group). Specific examples of the polymers having a nitrogen-containing basic functional group include polymers containing a vinyl derivative of a nitrogen-containing aromatic compound (e.g., vinylamine, 2-vinylpyridine, 4-vinylpyridine, 2-methyl-5-vinylpyridine, 4-vinylimidazole, N-vinyl-2-ethylimidazole, N-vinyl-2-methylimidazole); an acrylic or methacrylic acid derivative (e.g., dimethylaminoethyl (meth)acrylate, diethylaminoethyl (meth)acrylate, dimethylaminopropyl (meth)acrylate, 3-dimethylamino-2-hydroxypropyl (meth)acrylate); an acrylamide or methacrylamide derivative (e.g., N-dimethylaminoethyl (meth)acrylamide, N-diethylaminoethyl (meth)acrylamide); a styrene derivative (e.g., p-dimethylaminomethylstyrene, p-diethylaminoethylstyrene); and a vinyl compound derivative obtained by treating the above-enumerated vinyl compound with an alkyl halide to convert it to a quaternary ammonium salt.

Particularly preferred among them are those containing diethylaminoethyl (meth)acrylate, diethylaminoethyl (meth)acrylate, p-dimethylaminomethylstyrene, p-diethylaminoethylstyrene, etc.

The above-described polymer having a nitrogen-containing basic functional group is preferably a copolymer of a vinyl compound and a monomer containing a nitrogen-containing basic functional group, with the nitrogen content of the functional group in the polymer preferably ranging from 0.05 to 3.5% by weight, more preferably from 0.1 to 2.5% by weight.

The vinyl compound in the aforesaid copolymer includes alkyl (meth)acrylates (e.g., 2-hydroxyethyl methacrylate, methyl (meth)acrylate, ethyl (meth)acrylate, n-butyl (meth)acrylate), amides (e.g., (meth)acrylamide, N-methyl (meth)acrylamide); N-vinylpyrrolidone, vinyl acetate, styrene, etc.

The copolymers of the vinyl compound and the monomer having a nitrogen-containing basic functional group include block copolymers, grafted copolymers, random copolymers, and the like. Of them, grafted copolymers and block copolymers preferably have a micro-domain structure having an average length of from 100 Å to 100 μm in view of compatibility with blood.

Further, the copolymers of the vinyl compound and the monomer having a nitrogen-containing basic functional group are preferably random copolymers from the standpoint of facilitating the production and stability of the double-layered structure, and the compatibility with blood.

As the polymer having a nitrogen-containing basic functional group, 2-hydroxyethyl methacrylatediethylaminoethyl methacrylate copolymer is particularly preferred.

The terminology "double-layered structure" as used herein means a structure composed of a water-insoluble material as a core layer having coated thereon a blood-compatible polymer by a known coating method. The double-layered water-insoluble carrier may further be coated with a blood-compatible polymer of the same or different kind to have a multilayered structure. The double-layered structure is effective to prevent formation of fine particles of the water-insoluble material and to eliminate the safety problem of eluates from the water-insoluble material. Further, proper selection of the blood-compatible polymer can prevent formation of fine particles and further improves compatibility with blood. The multilayered structure further ensures prevention of fine particle formation and improvement on compatibility with blood.

The water-insoluble carrier may have any form, such as a particulate form, a fibrous form, a hollow yarn form, a membrane form, etc. From the standpoint of the amount of the ligand supportable and ease on handling of the adsorbent, a particulate or fibrous carrier is preferred. A spherical or particulate carrier has a mean particle size of from 25 to 2,500 $\mu$m, preferably from 50 to 1,500 $\mu$m in view of its specific surface area indicative of adsorptivity and the streamline of the body fluid to be treated. The carrier preferably has a specific surface area of at least 5 m$^2$/g, more preferably least 55 m$^2$/g.

The particulate carrier is preferably porous. The porous particles are such that the specified electrolyte can be fixed thereon. In order to increase adsorption efficiency, it is desirable that $\beta_2$-microglobulin enters deep into the pores of the porous particles. To this effect, the porous particles preferably have an average pore size ranging from 20 Å to 5,000 Å.

In the case of using the fibrous carrier, the fiber diameter is preferably from 0.02 to 10 deniers, more preferably from 0.1 to 5 deniers. Too large a fiber diameter reduces the adsorption and the rate of adsorption of $\beta_2$-microglobulin, and too small a fiber diameter tends to cause activation of the blood coagulation system, sticking of blood cells, or obstruction. The fibrous carrier to be used includes regenerated cellulose fibers, nylon fibers, acrylic fibers, polyester fibers and other known fibers.

The specified electrolyte can be fixed to the water-insoluble carrier by any of known processes, such as covalent bonding, ionic bonding, physical adsorption, embedding, and precipitation and insolubilization on the surface of the carrier. Taking possible elution of the electrolyte-carrier combination into consideration, the electrolyte is preferably fixed and insolubilized by covalent bonding. Covalent bonding can be effected by utilizing conventional methods for activating carriers and bonding ligands which are commonly employed in the field of immobilized enzyme and affinity chromatography.

Examples of the carrier activating methods include a cyanogen halide method, an epichlorohydrin method, a bisepoxide method, a triazine halide method, a bromoacetyl bromide method, an ethyl chloroformate method, a 1,1'-carbonyldiimidazole method, etc. With chemical and thermal stability being taken into consideration, methods of using an epoxide are preferred. The epichlorohydrin method is particularly recommended.

The methods for activating a water-insoluble carrier and bonding a ligand thereto are not limited to the above-described techniques. That is, fixation of the specified electrolyte on the carrier may also be carried out by a method in which a monomer providing the specified electrolyte is homo- or copolymerized in the presence of a crosslinking agent; a method in which a crosslinked polymer particle is post-crosslinked by using a crosslinking agent containing a monomer providing the specified electrolyte; a method in which an insoluble substance is coated with a polymer to which the specified electrolyte can be bonded and then bonding the electrolyte to the polymer; a method in which an insoluble substance is coated with a polymer containing a monomer providing the specified electrolyte and, if desired, post-crosslinking the polymer; or a method in which the specified electrolyte is activated and then bonded to a carrier.

If desired, a molecule of an arbitrary length (spacer), e.g., aminoethyl, aminopentyl, aminooctyl, and aminododecyl groups, may be introduced between the water-insoluble carrier and the electrolyte (ligand). The effect of the present invention is produced by the existence of the specified electrolyte as a ligand on the surface of the adsorbent and, therefore, does not depend on the method of production.

The double-layered water-insoluble carrier which comprises a water-insoluble material and a blood-compatible polymer can be prepared by any of known coating methods, such as spray coating, dip coating, and the like.

To take a concrete instance, the example of dip coating will be hereinafter described in detail. A blood-compatible polymer is dissolved in a solvent capable of uniformly dissolving the polymer to prepare a polymer solution that can easily be impregnated in or coated on the water-insoluble material. Basically, any kind of solvent is employable as long as it is capable of dissolving the polymer. A suitable solvent should be chosen so that it can be removed easily and a safety problem may not arise if it should remain in a trace amount. From these considerations, preferred solvents include lower alcohols (e.g., methanol, ethanol), acetone, diemthylformamide, and mixtures of these solvents with water.

A water-insoluble material having a desired particle size is dipped in the polymer solution in a nitrogen atmosphere at room temperature for about 5 minutes while occasionally stirring. After the excess of the solution is removed by suction through a glass filter, the insoluble material is dried in nitrogen on the glass filter for 20 minutes while adjusting the balance between the nitrogen feed and nitrogen suction. Then, the insoluble material is dried in a vacuum drier at room temperature at a pressure of 755 mm Hg or more for 24 hours.

A multilayered water-insoluble carrier having three or more layers can be prepared by repeatedly subjecting the thus-prepared double-layered carrier to the same procedure, i.e., dipping and drying. The blood-compatible polymer to be used here may be the same as or different from that used above.

Methods of using the $\beta_2$-microglobulin adsorbent of the present invention for cleaning body fluids are described below for illustrative purposes only but not for limitation.

The adsorbent of the present invention can be used either alone or as a mixture or a laminate with other body fluid cleaning materials. Other body fluid cleaning materials to be used in combination include activated carbon used in extra-corporal (artificial) kidney of the adsorption type, and a hollow yarn membrane or a flat membrane used in extra-corporal kidney of the dialysis type or filtration type. Such combinations are expected to produce synergistic effects to accomplish more extensive clinical effects. The volume of the adsorbent for use in vitro circulation suitably ranges from about 50 to about 600 ml.

Cleaning of the body fluids, e.g., blood, with the adsorbent by in vitro circulation can be carried out according to the following three methods. The first method comprises directly contacting whole blood taken from the body with the adsorbent to clean blood. The second method comprises separating the blood taken from the body into the plasma and the blood cells by means of a centrifuge or a membrane type plasma separator, contacting the plasma with the adsorbent, combining the thus-cleaned plasma with the blood cells, and returning the blood into the body. The third method comprises passing the blood taken from the body through a body fluid cleaning equipment, such as extra-corporal kidney of the adsorption type, dialysis type or filtration type and then contacting the thus-cleaned blood with the adsorbent. In the third method, the blood may be first brought into contact with the adsorbent and then passed through the body fluid cleaning equipment.

As the adsorbent of the invention exhibits markedly high adsorption performances, the particles of the adsorbent may be made large or the packing density of the adsorbent may be reduced while maintaining a high level of flow rate of the blood or plasma under treatment irrespective of the shape or form of the adsorbent. Therefore, a large quantity of body fluids can be treated with the adsorbent.

The contact of the body fluid such as blood or plasma with the adsorbent may be carried out continuously or intermittently according to clinical needs or situations of apparatus.

As described above, the adsorbent of the present invention adsorbs and removes $\beta_2$-microglobulin at a high efficiency and with specificity in a simple, easy, and safe way.

The present invention is applicable to general usages for cleaning and regenerating body fluids, such as blood and blood plasma and can be used effectively and safely for adsorption and removal of medium molecular weight substances and amyloid proteins, particularly $\beta_2$-microglobulin, which are found in high levels in the body fluids of patients suffering from renal insufficiency or malignant tumor and cause flexor canal syndrome, amyloidosis, digitus recellens, omarthritis, golarthritis, pruritus, bond involvement, etc.

The present invention is now illustrated in greater detail with reference to Reference Examples, Examples and Comparative Examples, but it should be understood that the present invention is not deemed to be limited thereto. In these examples, all of the percents and ratios are by weight unless otherwise indicated.

REFERENCE EXAMPLE 1

Various electrolytes according to the present invention were evaluated for the ability of binding to $\beta_2$-microglobulin fixed on the surface of a plastic plate (enzyme linked immunosorbent assay (ELISA) plate) by utilizing an enzymatic immunoassay commonly employed in clinical examinations. The method and conditions for the evaluation are set forth below.

1) Fixation of $\beta_2$-Microglobulin on ELISA Plate:

$\beta_2$-Microglobulin originating from human urine (available from Sigma Co.) was dissolved in phosphoric acid-buffered physiological saline (PBS) to prepare a PBS solution containing 10 $\mu$g/ml of $\beta_2$-microglobulin. A 100 $\mu$l portion of the solution was added to ELISA plate for enzymatic immunoassays ("Immulon 600" produced by C. A. Greiner und Sohne GmbH & CoKG) and left to stand at 4° C. for 24 hours.

2) Blocking of Free Surface of ELISA Plate:

The free surface of the ELISA plate where no $\beta_2$-microglobulin was fixed was blocked as follows in order to inhibit an electrolyte under test from binding thereto.

The $\beta_2$-microglobulin solution (100 $\mu$l) added to the plate in 1) above was removed therefrom by suction. Then, 200 $\mu$l of a 0.5% bovine serum albumin (BSA) solution in PBS was added to the ELISA plate, followed by allowing to stand at 25° C. for 2 hours.

3) Removal of Free BSA from ELISA Plate:

The free BSA solution on the ELISA plate was removed by suction, and 100 $\mu$l of PBS was added thereto. The PBS was removed by suction, and 100 $\mu$l of fresh PBS was added, followed by removal by suction. The washing with PBS was repeated three times to completely remove BSA remaining unfixed on the ELISA plate.

4) Binding of Electrolyte to $\beta_2$-Microglobulin:

Each of electrolytes shown in Tables 1 to 5 below was dissolved in PBS to prepare a solution containing 0.1 mg/ml of the electrolyte. After any PBS remaining on the ELISA plate was removed by suction in the above step 3), 100 $\mu$l of the electrolyte solution was added thereto and left to stand at 37° C. for 2 hours or, in the case of using collagen as an electrolyte, at 25° C. for 2 hours.

5) Removal of Free Electrolyte from ELISA Plate:

The free electrolytes PBS solution which was not bound to $\beta_2$-microglobulin was removed from the plate by suction. The ELISA plate was washed with PBS three times in the same manner as in 3) above to completely remove the free electrolyte therefrom.

6) Determination of $\beta_2$-Microglobulin Fixed on ELISA Plate and Unbound to Electrolyte:

The $\beta_2$-microglobulin which was fixed on the surface of the ELISA plate and was not bound to the electrolyte was determined in accordance with a usual enzymatic immunoassay as follows.

(a) After the procedure of 5), antihuman $\beta_2$-microglobulin rabbit antibody (100 $\mu$l) was added to the ELISA plate and allowed to stand at 37° C. for 1 hour or, in case of using collagen as an electrolyte, at 25° C. for 2 hours, followed by washing with PBS in the same manner as in 3) above. By this operation, the $\beta_2$-microglobulin which was not bound to the electrolyte underwent antigen-antibody reaction with antihuman $\beta_2$-microglobulin.

(b) Peroxidase-labeled anti-rabbit IgG (100 $\mu$l) (Bectustin ABC Kit) was then added to the plate to cause antigen-antibody reaction between the antihuman $\beta_2$microglobulin rabbit antibody and the anti-rabbit IgG.

(c) Thereafter, 0.2 mg/ml solution of 2,2'-Azino-bis-(3-ethylbenzothiazolin-6-sulfonic acid) (ABTS) (molecular weight: 514; 50 μl; produced by Wako Pure Chemical Ind., Ltd.) and 0.03%/ml aqueous hydrogen peroxide (50 μl) were added to the ELISA plate to thereby develop a color due to the peroxidase reaction. After the color development, the absorbance at a wavelength of 405 nm was measured. The measured adsorbance correlates to the amount of the antihuman $\beta_2$-microglobulin antibody bound to $\beta_2$-microglobulin.

Taking influences of the electrolyte itself on the above-described evaluation system into consideration, the operations from 2) through 6) were separately carried on, including no addition of $\beta_2$-microglobulin to ELISA plate. Further, the operations from 1) through 3) and 6) were separately carried on, including no addition of the electrolyte to ELISA plate.

Thus, a ratio (Y) of the $\beta_2$-microglobulin which was fixed on the surface of ELISA plate and unbound to the electrolyte to the total $\beta_2$-microglobulin which was fixed on the ELISA plate can be calculated from equation:

$$Y = \frac{(C)(D)}{(E)} \times 100\ (\%)$$

wherein (C) represents the amount of the antihuman $\beta_2$-microglobulin antibody having undergone antigen-antibody reaction, which is obtained by the operations from 1) through 5); (D) represents the amount of the antihuman $\beta_2$-microglobulin antibody having undergone antigen-antibody reaction, which is obtained by the operations from 2) through 5), including no addition of $\beta_2$-microglobulin to ELISA plate; and (E) represents the amount of the antihuman $\beta_2$-microglobulin antibody having undergone antigen-antibody reaction, which is obtained by the operations 1), 2), 3), and (6), including no addition of the electrolyte.

It can be understood that the smaller the Y value, the higher the ability of the electrolyte to bind to the $\beta_2$-microglobulin fixed on the ELISA plate. The results obtained are shown in Tables 1 to 5.

TABLE 1

| Polyamino Acid | Molecular Weight | X | Y |
|---|---|---|---|
| Poly-L-aspartic acid (produced by Seikagaku Kogyo Co., Ltd.) | 6,000 | 3.0 | 50.2 |
| Poly-L-glutamic acid | 55,000 | 4.0 | 54.3 |
| Poly(L-glutamic acid-alanine) (glutamic acid:alanine = 1:1) | 145,000 | 7.0 | 29.5 |
| Poly(L-glutamic acid-alanine-tyrosine) (glutamic acid:alanine:tyrosine = 1:1:1) | 60,000 | 7.5 | 30.1 |

TABLE 2

| Polysaccharide | Molecular Weight | X | Y |
|---|---|---|---|
| Diethylaminoethyl-dextran (made by Pharmacia Co., Sweden) | 500,000 | 3.3 | 40.2 |

TABLE 3

| Synthetic High Polymer | Molecular Weight | X | Y |
|---|---|---|---|
| Polymethacrylic acid | 70,000 | 3.0 | 60.2 |
| Styrene-maleic acid copolymer (styrene:maleic acid = 1:1, made by Aldrich Co., U.S.A.) | 50,000 | 5.0 | 19.8 |
| Carboxylated polyacrylamide (made by Polyscience Co., U.S.A.) | 200,000 | 6.0 | 40.2 |
| Sodium sulfonated polystyrene (made by Polyscience Co., U.S.A.) | 177,000 | 8.0 | 18.4 |
| Styrene-maleic acid copolymer (styrene:maleic acid = 3:1) | 3,000 | 13.0 | 21.1 |

TABLE 4

| Collagen | Molecular Weight | Isoelectric Point | X | Y |
|---|---|---|---|---|
| Methylated atelocollagen Type-I* (made by Koken Co., Ltd.) | 300,000 | 10.55 | 16.3 | 17.5 |

Note: *Prepared by treating collagen of bovine corium with pepsin and treating the resulting atelocollagen Type-I with methanol to methylate the carboxyl group thereof.

TABLE 5

| Gelatin | Molecular Weight | Isoelectric Point | X | Y |
|---|---|---|---|---|
| Acid-processed Gelatin* (made by Nippi Gelatin Kogyo Co., Ltd.) | 125,000 | 8.8 | 14.3 | 19.5 |
|  | 75,000 | 8.0 | 13.2 | 22.4 |
| Acid-processed gelatin* (made by Miyagi Kagaku Kogyo Co., Ltd.) | 100,000 | 9.3 | 11.8 | 23.2 |
| Enzyme-processed gelatin** (experimentally prepared by Asahi Kasei Kogyo Kabushiki Kaisha) | 85,000 | 6.9 | 10.8 | 35.2 |

Note:
*Prepared by processing the skin of pigs with an acid and heat-treating the resulting collagen under an acidic condition.
**Prepared by heat-treating atelocollagen Type-I (produced by Koken Co., Ltd.).

REFERENCE EXAMPLE 2

Electrolytes out of the scope of the present invention shown in Tables 6 and 7 were evaluated in the same manner as described in Reference Example 1. The results obtained are shown in the Tables.

TABLE 6

| Polysaccharide | Molecular Weight | X | Y |
|---|---|---|---|
| Dextran sulfate (made by Pharmacia Co., Sweden) | 500,000 | 1.66 | 81.2 |

TABLE 7

| Synthetic High Polymer | Molecular Weight | X | Y |
|---|---|---|---|
| Polyacrylic acid | 5,000 | 2.0 | 85.3 |
| Potassium polyvinyl sulfate (made by Wako Pure Chemical Ind., Ltd.) | 240,000 | 2.0 | 74.3 |
| Polyethyleneimine (made by Nakarai Kagaku Yakuhin Co., Ltd.) | 70,000 | 2.0 | 91.2 |

Figure 1:
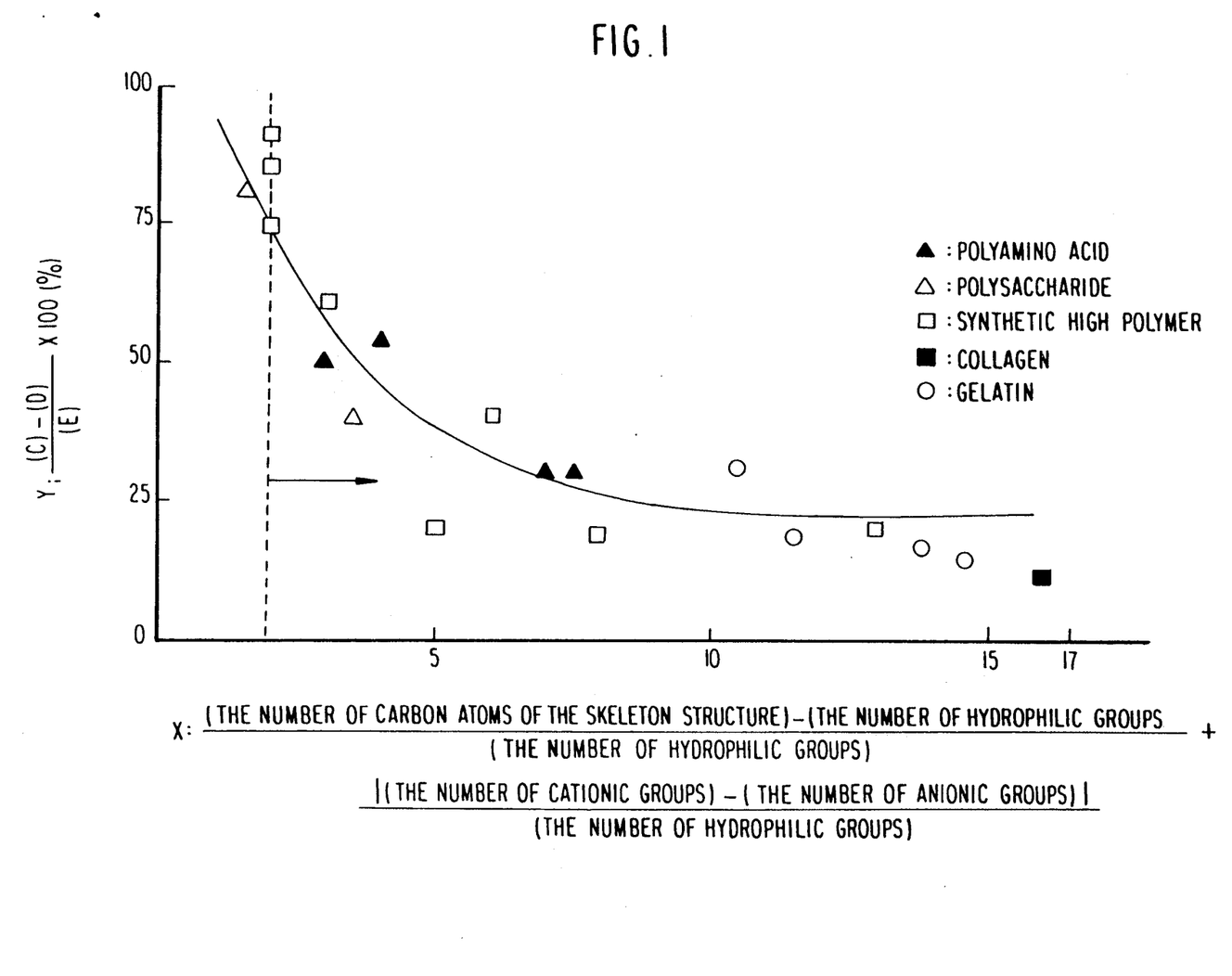
FIGS. 1 and 2 each is a graph showing a relationship between X values of the specified electrolytes and the ability of the binding to $\beta_2$-microglobulin thereto.

The results of Reference Examples 1 and 2 are inclusively depicted in FIG. 1, wherein Y is plotted as the ordinate and X as the abscissa. It can be seen from these results that the specified electrolytes of the present invention, which have X of more than 2.0, exhibit excellent ability of binding to $\beta_2$-microglobulin.

REFERENCE EXAMPLE 3

Sodium sulfonated polystyrenes having a varied molecular weight as shown in Table 8 below were evaluated in the same manner as in Reference Example 1. The results obtained are shown in the Table.

TABLE 8

| Molecular Weight | X | Y |
| --- | --- | --- |
| 1,800 | 8.0 | 45.2 |
| 4,600 | 8.0 | 37.1 |
| 18,000 | 8.0 | 26.2 |
| 100,000 | 8.0 | 19.9 |
| 177,000 | 8.0 | 18.4 |

REFERENCE EXAMPLE 4

Sodium sulfonated polystyrene having a molecular weight shown in Table 9 was evaluated in the same manner as in Reference Example 1. The results obtained are shown in the Table.

TABLE 9

| Molecular Weight | X | Y |
| --- | --- | --- |
| 800 | 8.0. | 85.3 |

Figure 2:
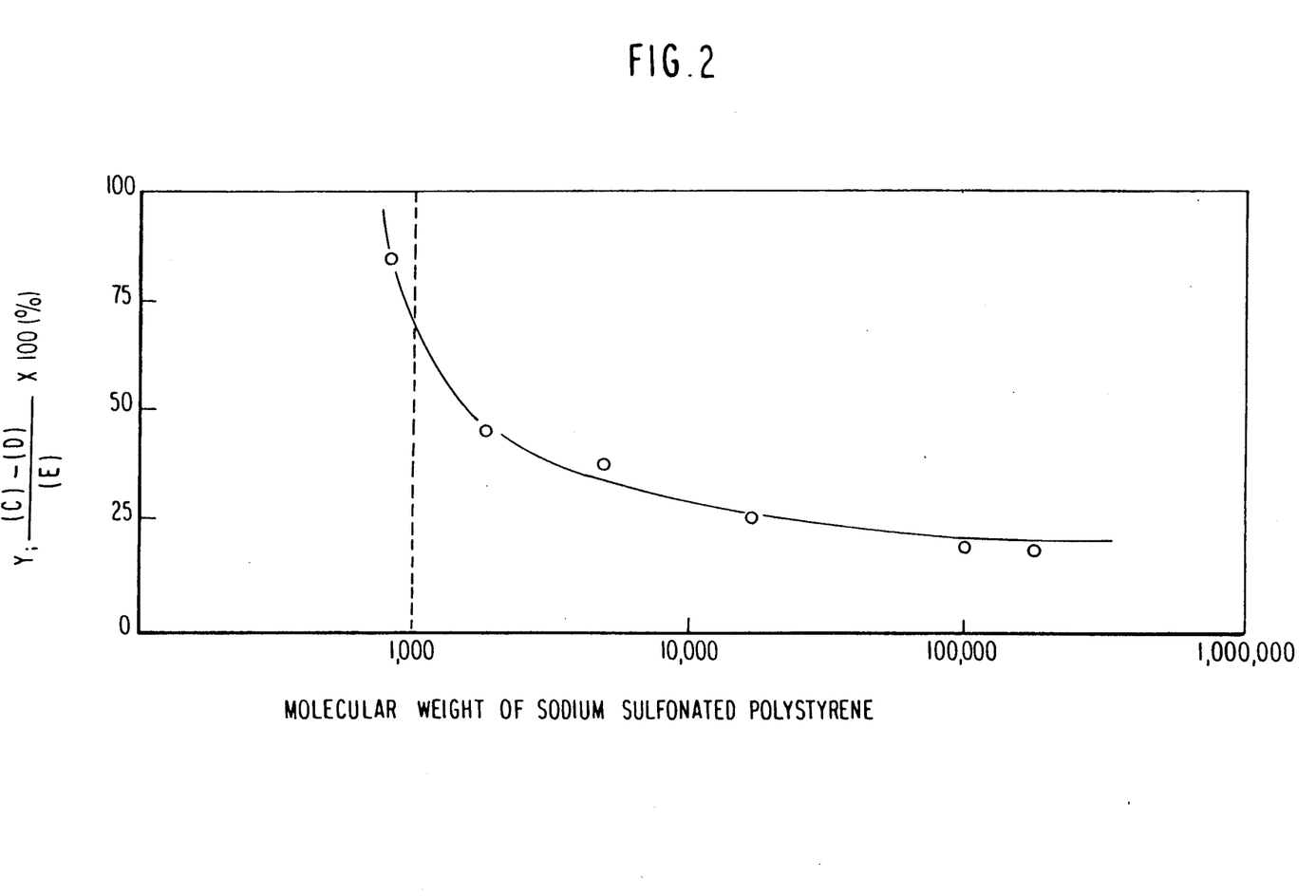

The results of Reference Examples 3 and 4 were inclusively depicted in FIG. 2, wherein Y was plotted as the ordinate and the molecular weight of sodium sulfonated polystyrene as the abscissa. It can be confirmed that satisfactory ability of electrolytes to bind to $\beta_2$-microglobulin can be exerted with their molecular weights being 1,000 or more.

EXAMPLE 1

Toyopearl HW-60 (particle size: 30 to 60 μm; produced by Toyo Soda Mfg. Co., Ltd.) was washed with water, dehydrated, and suspended in dimethyl sulfoxide (DMSO). The DMSO medium was removed, the particles again suspended in DMSO, and DMSO was removed. 30 ml of the thus-treated HW-60 were suspended in 36 ml of DMSO. To the suspension were added 24 ml of epichlorohydrin and 3.0 ml of a 50% sodium hydroxide aqueous solution, followed by stirring at 30° C. for 5 hours to effect activation reaction. After the reaction, the particles were washed successively with methanol and water and dehydrated by suction. The thus-activated HW-60 (30 ml) was divided into three 10 ml portions. Each portion was suspended in 50 ml each of a 3 mg/ml solution (pH =9.0) of poly-L-aspartic acid (molecular weight: 6,000), a 3 mg/ml solution (pH =9.0) of poly-(L-glutamic acid-alanine) (molecular weight: 145,000; L-glutamic acid:alanine =1:1) and a 3 mg/ml solution (pH =4.5) of a styrene-maleic acid copolymer (molecular weight: 50,000; styrene:maleic acid =1:1), respectively. The suspension was stirred at 50° C. for 14 hours to effect the fixation reaction. Thereafter, the particles were washed alternatingly with a 0.1 M sodium carbonate buffer (pH =9.0) and a 0.1 M sodium citrate buffer (pH =4.0) and then thoroughly washed successively with PBS and physiological saline to obtain an adsorbent.

The amount of poly-L-aspartic acid or poly-(L-glutamic acid-alanine) supported on the water-insoluble carrier was determined by reacting the primary amino group of these polyamino acids with 4-phenylspiro-(furan-2(3H),1'-phthalan)-3,3'-dione (Fluram-®<Roche> produced by F. Hoffmann-La Roche Limited Co. Limited). The amount of the styrene-maleic acid copolymer supported on the carrier was determined by measuring the absorbance of the benzene ring at a wavelength of 259.5 nm.

Each of the resulting adsorbents was evaluated for adsorptivity for $\beta_2$-microglobulin by an adsorption test as follows. Blood plasma separated from a blood sample of a patient suffering from renal insufficiency and the adsorbent or HW-60 (before fixation) were mixed at a volume ratio of 6:1, and the mixture was shaken at 37° C. for 1 hour. Concentrations of $\beta_2$-microglobulin and albumin before and after the adsorption test were determined by an RIA method and a BCG method, respectively. The blood plasma before adsorption had a $\beta_2$-microglobulin concentration of 25.5 mg/liter and an albumin concentration of 4.5 g/dl. The results obtained are shown in Table 10.

TABLE 10

| | Electrolyte | | | Concentration after Adsorption | |
| --- | --- | --- | --- | --- | --- |
| Kind | Amount Supported (mg/ml-adsorbent) | Molecular Weight | X | $\beta_2$-Microglobulin (mg/l) | Albumin (g/dl) |
| Poly-L-aspartic acid | 2.3 | 6,000 | 3.0 | 15.2 | 4.5 |
| Poly(L-glutamic acid-alanine) | 2.1 | 145,000 | 7.0 | 12.3 | 4.3 |
| Styrene-maleic acid copolymer | 3.4 | 50,000 | 5.0 | 10.2 | 4.4 |
| HW-60 (control) | 0 | — | — | 24.5 | 4.5 |

COMPARATIVE EXAMPLE 1

An adsorbent was prepared in the same manner as in Example 1, except for using a 3 mg/ml solution (pH=9.0) of poly-L-aspartic acid (molecular weight: 600) or a 3 mg/ml solution (pH=3.0) of polyacrylic acid (molecular weight: 5,000) as an electrolyte solution. Each of the adsorbents was tested in the same manner as in Example 1. The blood plasma before adsorption had a $\beta_2$-microglobulin concentration of 25.2 mg/liter and an albumin concentration of 4.5 g/dl. The results obtained are shown in Table 11.

TABLE 11

| | Electrolyte | | | Concentration after Adsorption | |
| --- | --- | --- | --- | --- | --- |
| Kind | Amount Supported (mg/ml-adsorbent) | Molecular Weight | X | $\beta_2$-Microglobulin (mg/l) | Albumin (g/dl) |
| Poly-L-aspartic acid | 3.2 | 600 | 3.0 | 23.4 | 4.5 |
| Polyacrylic acid | 3.4 | 5,000 | 2.0 | 22.5 | 4.4 |

TABLE 11-continued

| Kind | Electrolyte | | | Concentration after Adsorption | |
|---|---|---|---|---|---|
| | Amount Supported (mg/ml-adsorbent) | Molecular Weight | X | $\beta_2$-Microglobulin (mg/l) | Albumin (g/dl) |
| HW-60 before fixation | 0 | — | — | 24.5 | 4.5 |

From the results of Example 1 and Comparative Example 1, it is revealed that adsorbents having on the surface thereof an electrolyte having a molecular weight of 1,000 or more and X of more than 2.0 exhibit high adsorptivity for $\beta_2$-microglobulin with no adsorptivity for albumin.

REFERENCE EXAMPLE 5

Collagen shown in Table 12 below was evaluated in the same manner as in Reference Example 1. The results obtained are shown in Table 12.

TABLE 12

| Collagen | Molecular Weight | Isoelectric Point | X | Y |
|---|---|---|---|---|
| Atelocollagen Type-I* (made by Koken Co., Ltd.) | 300,000 | 9.10 | 11.7 | 85.7 |
| Succinated atelocollagen Type-I** (made by Koken Co., Ltd.) | 300,000 | 4.57 | 12.2 | 90.1 |

Note:
*Prepared by treating collagen of bovine corium with pepsin.
**Prepared by treating atelocollagen Type-I with succinic anhydride to succinylate the amino group thereof.

From the results Of Table 12 in view of Table 4 of Reference Example 1, it can be seen that collagen having an isoelectric point of 9.5 or more exhibits strong ability to bind to $\beta_2$-microglobulin.

EXAMPLE 2

30 ml of methyl methacrylate-divinylbenzene copolymer particles (80:20 by weight) having a particle size of from 420 to 800 μm and an air bubble contact angle of 65°±3° (in water) were immersed in 100 ml of a 2 wt/v% methanolic solution of a 2-hydroxyethyl methacrylate-diethylaminoethyl methacrylate copolymer for 5 minutes while occasionally stirring. The excess solution was removed by filtration by suction through a glass filter, and the particles on the glass filter were dried with nitrogen for 20 minutes while balancing between the nitrogen feed and the nitrogen suction. Then, the particles were dried in a vacuum drier udner conditions of room temperature and 755 mm Hg or higher for 24 hours. There was obtained a water-insoluble carrier having a double-layered structure composed of a methyl methacrylate-divinylbenzene copolymer and a 2-hydroxyethyl methacrylate-diethylaminoethyl methacrylate copolymer.

The resulting water-insoluble carrier was heat-treated at 125° C. for 45 minutes, suspended in ethanol, washed with water, dehydrated, and suspended in DMSO. The DMSO was removed, and the particles were again suspended in DMSO. 30 ml of the thus-treated water-insoluble carrier were suspended in 36 ml of DMSO, and 24 ml of epichlorohydrin and 3.0 ml of a 50% sodium hydroxide aqueous solution were added thereto, followed by stirring at 30° C. for 5 hours to effect the activation reaction. After the reaction, the activated carrier was washed successively with methanol and water and then dehydrated by suction.

In 150 ml of a 2 mg/ml solution (pH=8.0) of methylated atelocollagen Type-I (made by Koken Co., Ltd.) was suspended 30 ml of the activated water-insoluble carrier, and the mixture was shaken at 25° C. for 48 hours to effect fixation of the methylated atelocollagen on the carrier. The particles were washed alternatingly with a 0.1 M sodium carbonate buffer (pH=9.0) and a 0.1 M sodium citrate buffer (pH=4.0) and then thoroughly washed successively with PBS and physiological saline to obtain an adsorbent.

The amount of the methylated atelocollagen supported on the surface of the adsorbent was determined by reacting the primary amino group of the methylated atelocollagen with 4-phenylspiro(furan-2(3H),1'-phthalan)-3,3'-dione (Fluram®<Roche>).

Blood plasma taken from a patient suffering from renal insufficiency and the adsorbent or the water-insoluble carrier were mixed at a volume ratio of 24:1 and shaken at 25° C. for 1 hour. Concentrations of $\beta_2$-microglobulin and albumin before and after the adsorption were determined in the same manner as in Example 1. The results obtained are shown in Table 13. The concentrations of $\beta_2$-microglobulin and albumin in the blood plasma before adsorption were 45.2 mg/liter and 4.5 g/dl, respectively.

TABLE 13

| Water-Insoluble Carrier | | Electrolyte | | | | | Concentration after Adsorption | |
|---|---|---|---|---|---|---|---|---|
| Water-Insoluble Material | Blood-Compatible Polymer | Kind | Amount Supported (mg/ml-adsorbent) | Molecular Weight | X | Iso-electric Point | $\beta_2$-Micro-globulin (mg/l) | Albumin (g/dl) |
| Methyl methacrylate-divinylbenzene copolymer | 2-Hydroxyethyl methacrylate-diethylaminoethyl methacrylate copolymer | Methylated atelo-collagen Type-I | 3.5 | 300,000 | 16.3 | 10.55 | 15.4 | 4.3 |
| Methyl methacrylate-divinylbenzene copolymer | 2-Hydroxyethyl methacrylate-diethylaminoethyl methacrylate copolymer | None | 0 | — | — | — | 30.2 | 4.3 |

COMPARATIVE EXAMPLE 2

An adsorbent was prepared in the same manner as in Example 2, except for using a 2 mg/ml solution (pH=8.0) of atelocollagen Type-I (produced by Koken Co., Ltd.) having properties shown in Table 14 below. The results of the adsorption test carried out in the same manner as in Example 2 are shown in Table 14. The $\beta_2$-microglobulin and albumin concentrations before the adsorption were 45.2 mg/liter and 4.5 g/dl, respectively.

TABLE 14

| Kind | Electrolyte Amount Supported (mg/ml-adsorbent) | Molecular Weight | X | Isoelectric Point | Concentration after Adsorption $\beta_2$-Microglobulin (mg/l) | Albumin (g/dl) |
| --- | --- | --- | --- | --- | --- | --- |
| Atelocollagen Type-I | 3.4 | 300,000 | 11.7 | 9.10 | 28.1 | 4.3 |
| Insoluble carrier | 0 | — | — | — | 30.2 | 4.3 |

The results of Example 2 and Comparative Example 2 prove that the adsorbent having supported thereon collagen having an isoelectric point of 9.5 or more exhibits high adsorption performance for $\beta_2$-microglobulin with high selectivity.

REFERENCE EXAMPLE 6

Gelatin having properties shown in Table 15 was evaluated in the same manner as in Reference Example 1. The results obtained are shown in Table 15.

TABLE 15

| Gelatin | Molecular Weight | Isoelectric Point | X | Y |
| --- | --- | --- | --- | --- |
| Alkali-processed gelatin* (Nippi Gelatin Kogyo Co., Ltd.) | 125,000 | 5.0 | 12.0 | 91.6 |
| Alkali-processed gelatin* (Nippi Gelatin Kogyo Co., Ltd.) | 75,000 | 5.1 | 11.9 | 90.2 |
| Enyme-processed gelatin** (experimentally prepared by Asahi Kasei Kogyo Kabushiki Kaisha) | 80,000 | 6.3 | 11.3 | 74.5 |

Note:
*Prepared by processing cattle bones with an alkali and heat-treating the resulting collagen under an alkaline condition.
**Prepared by heat-treating atelocollagen Type-I (made by Koken Co., Ltd.).

It can be seen from Table 5 of Reference Example 1 and Table 15 of Reference Example 6 that gelatin having an isoelectric point of 6.5 or higher exhibits excellent ability of binding to $\beta_2$-microglobulin.

REFERENCE EXAMPLE 7

Gelatin having properties shown in Table 16 was evaluated in the same manner as in Reference Example 1. The results obtained are shown in Table 16.

TABLE 16

| Gelatin | Molecular Weight | Isoelectric Point | X | Y |
| --- | --- | --- | --- | --- |
| Acid-processed gelatin* (experimentally prepared by Asahi Kasei Kogyo Kabushiki Kaisha) | 50,000 | 8.2 | 13.4 | 30.4 |
| | 10,000 | 8.1 | 13.3 | 35.2 |
| | 7,000 | 7.0 | 11.0 | 38.5 |
| | 1,500 | 7.0 | 11.0 | 41.2 |
| | 800 | 6.9 | 10.8 | 72.3 |

Note: *Prepared by heat-treating the acid-processed gelatin used in Reference Example 1 (molecular weight: 125,000; isoelectric point: 8.8; X: 14.3; Y: 19.5; produced by Nippi Gelatin Kogyo Co., Ltd.).

It can be seen from Table 16 that gelatin having a molecular weight of 1,000 or more exhibits satisfactory ability of binding to $\beta_2$-microglobulin.

EXAMPLE 3

30 ml of methyl methacrylate-divinylbenzene copolymer particles (80:20 by weight) having a particle size of from 420 to 800 μm and an air bubble contact angele of 65±3° (in water) were immersed in 100 ml of a 2 wt/v% methanolic solution of a 2-hydroxyethyl methacrylate-diethylaminoethyl methacrylate copolymer for 5 minutes while occasionally stirring. The excess solution was removed by filtration by suction through a glass filter, and the particles on the glass filter were dried with nitrogen for 20 minutes while balancing between the nitrogen feed and the nitrogen suction. Then, the particles were dried in a vacuum drier under conditions of room temperature and 755 mm Hg or higher for 24 hours. There was obtained a water-insoluble carrier having a double-layered structure composed of a methyl methacrylate-divinylbenzene copolymer and a 2-hydroxyethyl methacrylate-diethylaminoethyl methacrylate copolymer.

The resulting water-insoluble carrier was heat-treated at 125° C. for 45 minutes, suspended in ethanol, washed with water, dehydrated, and suspended in dimethyl sulfoxide. The dimethyl sulfoxide was removed, and the particles were again suspended in dimethyl sulfoxide. 30 ml of the thus-treated carrier were suspended in 36 ml of dimethyl sulfoxide, and 24 ml of epichlorohydrin and 3.0 ml of a 50% sodium hydroxide aqueous solution were added thereto, followed by stirring at 30° C. for 5 hours to effect the activation reaction. After the reaction, the activated carrier was washed successively with methanol and water and then dehydrated by suction.

The resulting activated water-insoluble carrier (30 ml) was suspended in 150 ml of a 20.0 mg/ml solution (pH=3.5) of acid-processed gelatin having properties shown in Table 17, and the mixture was shaken at 30° C. for 48 hours to thereby fix the gelatin to the carrier.

The particles were washed alternatingly with a 0.1 M sodium carbonate buffer (pH=9.0) and a 0.1 M sodium citrate buffer (pH=4.0) and then thoroughly washed successively with PBS and physiological saline to obtain an adsorbent.

The amount of the acid-processed gelatin supported on the carrier was determined by a microbiuret method utilizing biuret reaction of proteins (cf. H. Yuki (ed.), *SEIKAGAKU BUNSEKIHO*, 123–125, Nankodo (1984)).

A blood plasma sample taken from a patient suffering from renal insufficiency and the above-preapred adsorbent or the water-insoluble carrier were mixed at a volume ratio of 24:1, followed by shaking at 37° C. for 1 hour. Concentrations of $\beta_2$-microglobulin and albumin before and after the adsorption were determined by an RIA method and a BCG method in the same manner as in Reference Example 1, respectively. The results obtained are shown in Table 17. The $\beta_2$-microglobulin and albumin concentrations before the adsorption were 45.2 mg/liter and 4.5 g/dl, respectively.

EXAMPLE 4

30 ml of methyl methacrylate-divinylbenzene copolymer particles (80:20 by weight) having a particle size of from 420 to 800 μm and an air bubble contact angle of 65°±3° (in water) were immersed in 100 ml of a 2 wt/v% methanolic solution of a 2-hydroxyethyl methacrylate-diethylaminoethyl methacrylate copolymer for 5 minutes while occasionally stirring. The excess solution was removed by filtration by suction through a glass filter and the particles on the glass filter were dried with nitrogen for 20 minutes while balancing between the nitrogen feed and the nitrogen suction. Then, the particles were dried in a vacuum drier under conditions

TABLE 17

| Water-Insoluble Carrier | | Electrolyte | | | | | | Concentration after Adsorption | |
|---|---|---|---|---|---|---|---|---|---|
| Water-Insoluble Material | Blood-Compatible Polymer | Kind | Amount Supported (mg/ml-adsorbent) | Molecular Weight | X | Y | Isoelectric Point | $\beta_2$-Microrglobulin (mg/l) | Albumin (g/dl) |
| Methyl methacrylate-divinylbenzene copolymer | 2-Hydroxyethyl methacrylate-diethylaminoethyl methacrylate copolymer | Acid-processed gelatin* Type-I | 45.3 | 75,000 | 13.2 | 22.4 | 8.0 | 15.7 | 4.3 |
| Methyl methacrylate-divinylbenzene copolymer | 2-Hydroxyethyl methacrylate-diethylaminoethyl methacrylate copolymer | Acid-processed gelatin** | 39.5 | 7,000 | 11.0 | 38.5 | 7.0 | 19.6 | 4.3 |
| Methyl methacrylate-divinylbenzene copolymer | 2-Hydroxyethyl methacrylate-diethylaminoethyl methacrylate copolymer | None | 0 | — | — | — | — | 30.2 | 4.3 |

Note:
*Produced by Nippi Gelatin Kogyo Co., Ltd.
**Produced by Asahi Kasei Kogyo Kabushiki Kaisha on an experimental basis

COMPARATIVE EXAMPLE 3

An adsorebnt was prepared in the same manner as in Example 3, except for using a 20.0 mg/ml solution (pH=3.5) of gelatin shown in Table 18. The results of the adsorption test carried out in the same manner as in Example 3 are shown in Table 18. The $\beta_2$-microglobulin and albumin concentrations before the adsorption were 45.2 mg/liter and 4.5 g/dl, respectively.

of room temperature and 755 mm Hg or higher for 24 hours. There was obtained a water-insoluble carrier having a double-layered structure composed of a methyl methacrylate-divinylbenzene copolymer and a 2-hydroxyethyl methacrylate-diethylaminoethyl methacrylate copolymer.

The resulting water-insoluble carrier was heat-treated at 125° C. for 45 minutes, suspended in ethanol, washed with water, dehydrated, and suspended in

TABLE 18

| | Electrolyte | | | | | Concentration after Adsorption | |
|---|---|---|---|---|---|---|---|
| Kind | Amount Supported (mg/ml-adsorbent) | Molecular Weight | X | Y | Isoelectric Point | $\beta_2$-Microglobulin (mg/ml) | Albumin (g/dl) |
| Alkali-processed gelatin* | 38.5 | 75,000 | 11.9 | 90.2 | 5.1 | 28.2 | 4.3 |
| Acid-processed gelatin** | 43.3 | 800 | 10.8 | 72.3 | 6.9 | 29.7 | 4.3 |
| Insoluble carrier | 0 | — | — | — | — | 30.2 | 4.3 |

Note:
*Produced by Nippi Gelatin Kogyo Co., Ltd.
**Prepared by Asahi Kasei Kogyo Kabushiki Kaisha on an experimental basis.

It can be seen from hte results of Example 3 and Comparative Example 3 that an adsorbent having supported thereon gelatin having a molecular weight of 1,000 or more and an isoelectric point of 6.5 or more exhibits high adsorptivity for $\beta_2$-microglobulin with high selectivity.

DMSO. The DMSO was removed, and the particles were again suspended in DMSO. 30 ml of the thus-treated water-insoluble carrier were suspended in 36 ml of DMSO and 24 ml of epichlorohydrin and 3.0 ml of a 50% sodium hydroxide aqueous solution were added thereto, followed by stirring at 30° C. for 5 hours to effect the activation reaction. After the reaction, the activated carrier was washed successively with methanol and water and then dehydrated by suction.

The resulting activated water-insoluble carrier (30 ml) was suspended in 150 ml of a 3 mg/ml solution (pH=4.5) of a styrene-maleic acid copolymer (styrene:maleic acid =1:1; molecular weight: 50,000), and the suspension was stirred at 50° C. for 14 hours to fix the copolymer on the carrier. The particles were washed alternatingly with a 0.1 M sodium carbonate buffer (pH=9.0) and a 0.1 M sodium citrate buffer (pH=4.0) and then thoroughly washed successively with PBS and physiological saline to obtain an adsorbent.

The amount of the styrene-maleic acid copolymer supported on the carrier was determined by measuring the absorbance of the benzene ring at a wavelength of 259.5 nm.

A blood plasma sample taken from a patient suffering from renal insufficiency and the adsorbent or the water-insoluble carrier were mixed at a volume ratio of 24.1, followed by shaking at 37° C. for 1 hour. The concentrations of $\beta_2$-microglobulin and albumin before and after tne adsorption were determined by an RIA method and a BCG method in the same manner as in Example 1, respectively, and the results are shown in Table 19. The $\beta_2$-microglobulin and albumin concentrations before the adsorption were found to be 45.2 mg/liter and 4.5 g/dl, respectively.

Further, the adsorbent was evaluated for compatibility with blood by determining permeation to blood platelets as follows.

(a) Preparation of Column for Evaluation:

Tne adsorbent was packed in a cylindrical column (diameter: 5 mm $\phi$; length: 10 mm) fitted with a polyester mesh (80 mesh) at the inlet and outlet thereof while passing physiological saline at a degree of vacuum of from 200 to 300 mm Hg. The column packed with the adsorbent was left to stand for 16 hours.

(b) Passage of Human Blood and Determination of Permeability to Platelets:

Heparin-added physiological saline (heparin concentration: 1 unit/ml) was passed through the column (column content: 0.2 ml) at a rate of 0.1 ml/min by means of a syringe type micropump. Then, heparin-added human blood collected from peripheral veins (heparin concentration: 15 unit/ml) was passed through the column at room temperature (20° C.) at a rate of 0.1 ml/min. The time point when the physiological saline in the column was pushed out of the column from the outlet was taken as zero time. The blood was collected from the column outlet in a sample containing sodium ethylenediaminetetraacetate. Within 2 hours from the sampling, the number of the blood platelets at the inlet and that at the outlet were measured according to the Brecher-Cronkite method. The permeability (%) of the column to blood platelets can be calculated by equation:

Permeability to Blood Platelet (%) =

$$\frac{\text{Number of Platelets at outlet}}{\text{Number of Platelets at Inlet}} \times 100$$

The results obtained are also shown in Table 19.

TABLE 19

| Water-Insoluble Carrier | | | Electrolyte | | | Concentration after Adsorption | | Permeability to Blood Platelets (%) | | | |
|---|---|---|---|---|---|---|---|---|---|---|---|
| Water-Insoluble Material | Contact Angle (°) | Blood-Compatible Polymer | Kind | Amount Supported (mg/ml-adsorbent) | Molecular Weight | X | $\beta_2$-Microglobulin (mg/l) | Albumin (g/dl) | 10–12 Min | 18–20 Min | 26–28 Min | $\bar{x}$ |
| Methyl methacrylate-divinylbenzene copolymer | 65 ± 3 | 2-Hydroxyethyl methacrylate-diethylaminoethyl methacrylate copolymer | Styrene-maleic acid copolymer | 3.5 | 50,000 | 5.0 | 15.4 | 4.4 | 83.5 | 80.6 | 74.3 | 79.4 |

From the foregoing examples, it can be understood that the adsorbent according to the present invention which comprises a water-insoluble carrier having supported thereon as a ligand at least one electrolyte selected from the group consisting of polyamino acids, polysacchardies, synthetic high polymers, collagen having an isoelectric point of 9.5 or more, and gelatin having an isoelectric point of 6.5 or more, each of which has a molecular weight of 1,000 or more and X of more than 2.0 exhibit highly efficient and specific adsorptivity for $\beta_2$-microglobulin without showing adsorptivity for albumin. Moreover, the adsorbent in which the water-insoluble carrier has a double-layered structure composed of a water-insoluble material having a contact angle (a contact angle with an air bubble in water) of at least 20° and a blood-compatible polymer is preferred particularly for use in cleaning whole blood.

While the invention has been described in detail and with reference to specific embodiments thereof, it will be apparent to one skilled in the art that various changes and modifications can be made therein without departing from the spirit and scope thereof.

What is claimed is:

1. An adsorbent for $\beta_2$-microglobulin which comprises a water-insoluble carrier having supported thereon, as a ligand, at least one electrolyte selected from the group consisting of a polyamino acid, a polysaccharide, a synthetic high polymer, collagen having an isoelectric point of 9.5 or more, and gelatin having an isoelectric point of 6.5 or more, wherein said electrolyte contains at least one group exhibiting a positive or negative charge in a neutral electrolytic solution and has a molecular weight of not less than 1,000 and an X value or more than 2.0, wherein X is a relationship regarding the skeleton structure of said electrolyte and is the sum of A and B, wherein A represents (the number of carbon atoms of the skeleton structure)−(the number of hydrophilic groups)/(the number of hydrophilic groups); and B represents |(the number of cationic groups)−(the number of anionic groups)|/(the number of hydrophilic groups).

2. The adsorbent for $\beta_2$-microglobulin as claimed in claim 1, wherein said ligand is at least one electrolyte selected from the group consisting of a polyamino acid, a polysaccharide and a synthetic high polymer.

3. The adsorbent for $\beta_2$-microglobulin as claimed in claim 2, wherein said ligand has a molecular weight of from 1,000 to 1,000,000.

4. The adsorbent for $\beta_2$-microglobulin as claimed in claim 2, wherein said ligand has an X value of from greater than 2 but not more than 15.

5. The adsorbent for $\beta_2$-microglobulin as claimed in claim 2, wherein said ligand is a polyamino acid electrolyte.

6. The adsorbent for $\beta_2$-microglobulin as claimed in claim 5 wherein said polyamino acid electrolyte is poly(glutamic acid-alanine) or poly-(glutamic acid-alanine-tyrosine).

7. The adsorbent for $\beta_2$-microglobulin as claimed in claim 2, wherein said ligand is a polysaccharide electrolyte.

8. The absorbent for $\beta_2$-microglobulin as claimed in claim 7, wherein said polysaccharide electrolyte is diethylaminoethyl-dextran.

9. The adsorbent for $\beta_2$-microglobulin as claimed in claim 1, wherein said ligand is a synthetic high polymer electrolyte.

10. The adsorbent for $\beta_2$-microglobulin as claimed in claim 9, wherein said synthetic high polymer electrolyte is sodium sulfonated polystyrene or styrene-maleic acid copolymer.

11. The adsorbent for $\beta_2$-microglobulin as claimed in claim 1, wherein said water-insoluble carrier has a double-layered structure composed of a water-insoluble material having a contact angle with air bubble in water of at least 20° and a polymer compatible with blood.

12. The adsorbent for $\beta_2$-microglobulin as claimed in claim 11, wherein said water-insoluble material is an organic polymer.

13. The adsorbent for $\beta_2$-microglobulin as claimed in claim 11, wherein said water-insoluble material has a contact angle with air bubble in water of at least 40°.

14. The adsorbent for $\beta_2$-microglobulin as claimed in claim 11, wherein said polymer compatible with blood is a polymer having a nitrogen-containing basic functional group.

15. The adsorbent for $\beta_2$-microglobulin as claimed in claim 14, wherein said polymer having a nitrogen-containing basic functional group is 2-hydroxyethyl methacrylate-diethylaminoethyl methacrylate copolymer.

16. The adsorbent for $\beta_2$-microglobulin as claimed in claim 1, wherein said water-insoluble carrier is activated using an epoxide.

17. The adsorbent for $\beta_2$-microglobulin as claimed in claim 1, wherein said water-insoluble carrier is activated using an epichlorohydrin.

18. The adsorbent for $\beta_2$-microglobulin as claimed in claim 1, wherein said ligand is a collagen electrolyte.

19. The absorbent for $\beta_2$-microglobulin as claimed in claim 18, wherein said collagen electrolyte is methylated atelocollagen Type-I.

20. The adsorbent for $\beta_2$-microglobulin as claimed in claim 1, wherein said ligand is a gelatin electrolyte.

21. The adsorbent for $\beta_2$-microglobulin as claimed in claim 20, wherein said gelatin electrolyte is an electrolyte obtained by the heat treatment under an acidic condition of collagen obtained by treating under an acidic condition.

22. The adsorbent for $\beta_2$-microglobulin as claimed in claim 1, wherein said ligand is a collagen or gelatin electrolyte.

23. The adsorbent for $\beta_2$microglobulin as claimed in claim 22, wherein said collagen or gelatin electrolyte has molecular weight of from 10,000 to 500,000.

24. The adsorbent for $\beta_2$-microglobulin as claimed in claim 22, wherein said collagen or gelatin electrolyte has an X value for from greater than 2 but not more than 25.

25. A method for cleaning or regenerating a body fluid derived from patients suffering from renal insufficiency or malignant tumor which comprises contacting said body fluid taken from the body with the adsorbent defined in claim 1, adsorbing and removing $\beta_2$-microglobulin at a high efficiency and with specificity, and then returning the cleaned body fluids into the body.

26. The method as claimed in claim 25, wherein said body fluid is blood, plasma, serum, ascites or hydrothorax.

* * * * *